(12) United States Patent
Gunderson (10) Patent No.: US 7,266,409 B2
(45) Date of Patent: Sep. 4, 2007

(54) METHOD AND APPARATUS FOR DETERMINING OVERSENSING IN A MEDICAL DEVICE

(75) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 251 days.

(21) Appl. No.: 11/107,533

(22) Filed: Apr. 15, 2005

(65) Prior Publication Data

US 2006/0116730 A1    Jun. 1, 2006

Related U.S. Application Data

(60) Provisional application No. 60/632,000, filed on Dec. 1, 2004.

(51) Int. Cl.
    *A61B 5/0402* (2006.01)
(52) U.S. Cl. ............... 600/515; 607/9; 607/4; 600/518; 600/509
(58) Field of Classification Search .......... 607/27, 607/2–5, 9; 600/515, 518, 509
    See application file for complete search history.

(56) References Cited

U.S. PATENT DOCUMENTS

| | | | |
|---|---|---|---|
| 4,374,382 A | 2/1983 | Markowitz | 340/870.01 |
| 4,428,378 A | 1/1984 | Anderson et al. | 128/419 PG |
| 4,913,146 A | 4/1990 | Decote, Jr. | |
| 5,107,833 A | 4/1992 | Barsness | 128/419 PT |
| 5,117,824 A | 6/1992 | Keimel et al. | 128/419 D |
| 5,168,871 A | 12/1992 | Grevious | 128/419 PT |
| 5,292,343 A | 3/1994 | Blanchette et al. | 607/32 |
| 5,314,450 A | 5/1994 | Thompson | 607/32 |
| 5,324,315 A | 6/1994 | Grevious | 607/60 |
| 5,354,319 A | 10/1994 | Wyborny et al. | 607/32 |
| 5,383,909 A | 1/1995 | Keimel | 607/7 |
| 5,545,186 A | 8/1996 | Olson et al. | 607/14 |
| 5,755,736 A | 5/1998 | Gillberg et al. | 607/4 |
| 6,155,267 A | 12/2000 | Nelson | |
| 7,167,747 B2 * | 1/2007 | Gunderson et al. | 607/9 |
| 2004/0230233 A1 | 11/2004 | Gunderson et al. | |

OTHER PUBLICATIONS

U.S. Appl. No. 10/436,626, filed May 13, 2003, entitled "Identification of Oversensing Using Sinus R-Wave Template" to Gunderson et al.

* cited by examiner

*Primary Examiner*—Kennedy J. Schaetzle
(74) *Attorney, Agent, or Firm*—Michael C. Soldner (57) ABSTRACT

A method and apparatus for determining oversensing in an implantable medical device that includes sensing a first cardiac signal and detecting cardiac events via a first electrode configuration, determining the presence of an episode requiring therapy in response to the detected cardiac events, sensing the first cardiac signal via a second electrode configuration, determining a baseline measurement of samples of the first cardiac signal sensed via the second electrode configuration, and determining whether to deliver therapy in response to the baseline measurement.

19 Claims, 7 Drawing Sheets

METHOD AND APPARATUS FOR DETERMINING OVERSENSING IN A MEDICAL DEVICE

RELATED APPLICATION

The present invention claims priority and other benefits from U.S. Provisional Patent Application Ser. No. 60/632,000, filed Dec. 1, 2004, entitled "IDENTIFICATION OF OVERSENSNING IN A MEDICAL DEVICE", incorporated herein by reference in its entirety. Cross-reference is hereby made to commonly assigned related U.S. patent application Ser. No. 10/436,626, filed May 13, 2003 now U.S. Pat. No. 7,167,747, incorporated herein by reference in its entirety.

FIELD OF THE INVENTION

The present invention generally relates to implantable medical devices, and more particularly relates to reducing effects of oversensing in implantable medical devices.

BACKGROUND OF THE INVENTION

Implantable medical devices (IMDs) have many functions including the delivery of therapies to cardiac patients, neuro-stimulators, muscular stimulators, and others. Application of the present invention is described below in the context of implantable cardiac pacemakers and/or defibrillators, it being understood that the principles herein may have applicability to other implantable medical devices as well.

An example of an implantable medical device (IMD) includes a device commonly referred to as a pacemaker, which is used to stimulate the heart into a contraction if the sinus node of the heart is not properly timing, or pacing, the contractions of the heart. Modern implantable medical devices also perform many other functions beyond that of pacing. For example, a pacemaker/cardioverter/defibrillator (PCD) performs therapies such as defibrillation and cardioversion as well as providing several different pacing therapies, depending upon the needs of the user and the physiologic condition of the user's heart.

In typical use, a PCD is implanted in a convenient location usually under the skin of the user and in the vicinity of the one or more major arteries or veins. One or more electrical leads connected to the PCD are inserted into or on the heart of the user, usually through a convenient vein or artery. The ends of the leads are placed in contact with the walls or surface of one or more chambers of the heart, depending upon the particular therapies deemed appropriate for the user.

One or more of the leads is adapted to carry a current from the PCD to the heart tissue to stimulate the heart in one of several ways, again depending upon the particular therapy being delivered. The leads are simultaneously used for sensing the physiologic signals provided by the heart to determine when to deliver a therapeutic pulse to the heart, and the nature of the pulse, e.g., a pacing pulse or a defibrillation shock.

In the sensing mode, sense amplifiers coupled to the leads provide amplification to electrogram signals picked up by the sensing electrodes in the heart. The analysis of these signals by the PCD determines whether a therapy (a pacing pulse or a defibrillator shock) should be administered. If erroneous signals are detected by the PCD, an unnecessary therapy may be administered, providing an unnecessary pacing pulse or defibrillator shock to the patient. One cause of erroneous interpretation of sensing signals is oversensing, that is, the false detection of a depolarization event.

Sensing can be accomplished in a number of ways. If two bipolar leads are used, one lead is typically placed within the right ventricle of the heart and a second lead is placed within the right atrium of the heart. Both leads include two sensing elements: a tip electrode that is attached to the wall or surface of the heart, and a ring electrode that is located on the lead but removed some distance from the tip electrode. A high voltage coil located on one or both of the leads can also be used for sensing, as can the implanted PCD can itself. Some cardiac conditions require sensing at both the right ventricle and the right atrium, and still others may add sensing at the left ventricle via a third lead positioned within the coronary sinus. As a result, there are a large number of sensing paths and combinations available for use, depending upon the configuration and programming of the specific implantable device, and some PCDs can be configured to switch to an alternate sensing path if the primary path is determined to be faulty.

Oversensing of cardiac waves may be caused by lead fractures (e.g., conductor break, insulation break, adaptor failure), connectors (e.g. loose set screw), T-wave oversensing, R-wave oversensing, electromagnetic interference (EMI), and myopotentials. In the past, oversensing problems (e.g., myopotentials, T-wave oversensing) have been dealt with by modifying sense amplifiers, filters and PCD lead electrodes. In currently used PCDs the sense amplifiers have self adjusting sensing thresholds for sensitivity, so oversensing often occurs as a result of lead failure. Upon detection of an R-wave, the threshold of the sense amplifier is raised to about 75% of the R-wave. The sense amplifier threshold then decays until the next R-wave is sensed. In this manner the sensing threshold of the sense amplified is continually adjusted to allow for variations in the sensed strength of the R-wave. However, there is still room for improved techniques for eliminating the effects of oversensing.

Accordingly, it is desirable to provide an additional mechanism for dealing with oversensing of depolarization events. In addition, it is desirable to provide an algorithm to be incorporated into detection algorithms in the IMD to prevent the detection and erroneous application of therapies for detected episodes caused by oversensing. Furthermore, other desirable features and characteristics of the present invention will become apparent from the subsequent detailed description and the appended claims, taken in conjunction with the accompanying drawings and the foregoing technical field and background.

BRIEF DESCRIPTION OF THE DRAWINGS

Aspects of the present invention will be readily appreciated as they become better understood by reference to the following detailed description when considered in connection with the accompanying drawings, wherein.

DETAILED DESCRIPTION OF THE INVENTION

Figure 1:
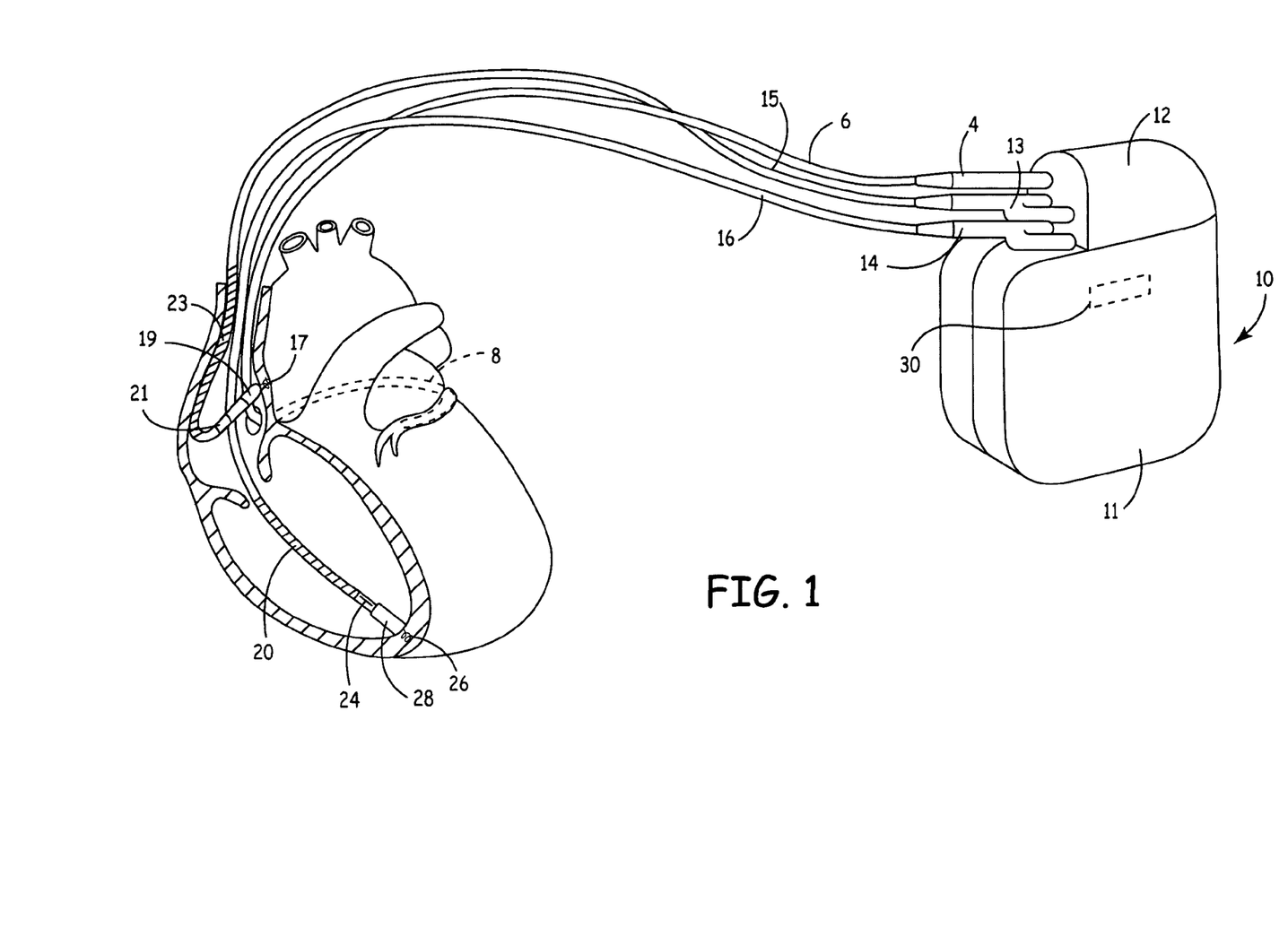
FIG. 1 is a schematic diagram of a pacemaker/cardioverter/defibrillator and lead set of a type in which the present invention may usefully be practiced.

FIG. 1 is a schematic diagram of a pacemaker/cardioverter/defibrillator and lead set of a type in which the present invention may usefully be practiced. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14, which carries three electrical connectors, each coupled to one of the coiled conductors.

The atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13, which carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 that carries an electrical connector, coupled to the coiled conductor.

The pacemaker/cardioverter/defibrillator 10 includes a hermetic enclosure or housing 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors 4, 13 and 14 and interconnecting the leads to the circuitry within housing 11. An optional sensor 30 is illustrated schematically by broken outline, and may include one or more of an activity sensor, respiration sensor (potentially from impedance), accelerometer-based posture detector, heart rate detector, ischemia detector and other available physiological sensor known in the art for measuring heart hemodynamics and may be a piezoelectric transducer as known in the art. Sensor 30 may be used, for example, to regulate the underlying pacing rate of the device in rate responsive pacing modes.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 2:
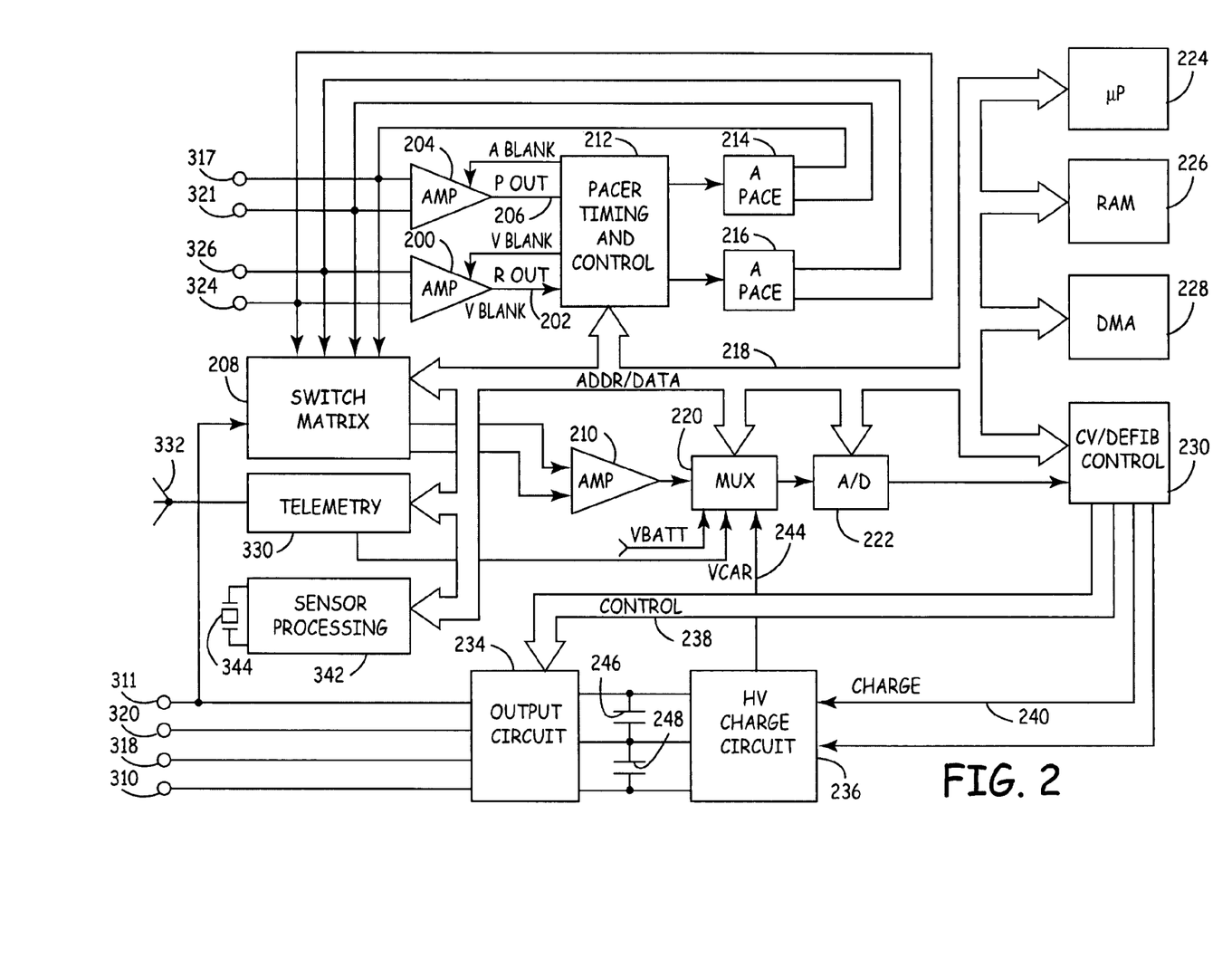
FIG. 2 is a functional schematic diagram of an implantable pacemaker/cardioverter/defibrillator of the type illustrated in FIG. 1, in which the present invention may usefully be practiced.

FIG. 2 is a functional schematic diagram of an implantable pacemaker/cardioverter/defibrillator of the type illustrated in FIG. 1, in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to an electrode formed along the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A v-sense signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 2 includes an optional activity sensor 344, mounted to the interior surface of the device housing or to the hybrid circuit within the device housing and corresponds to sensor 30 of FIG. 1. The sensor 344 and sensor present in circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention to determine oversensing and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 3:
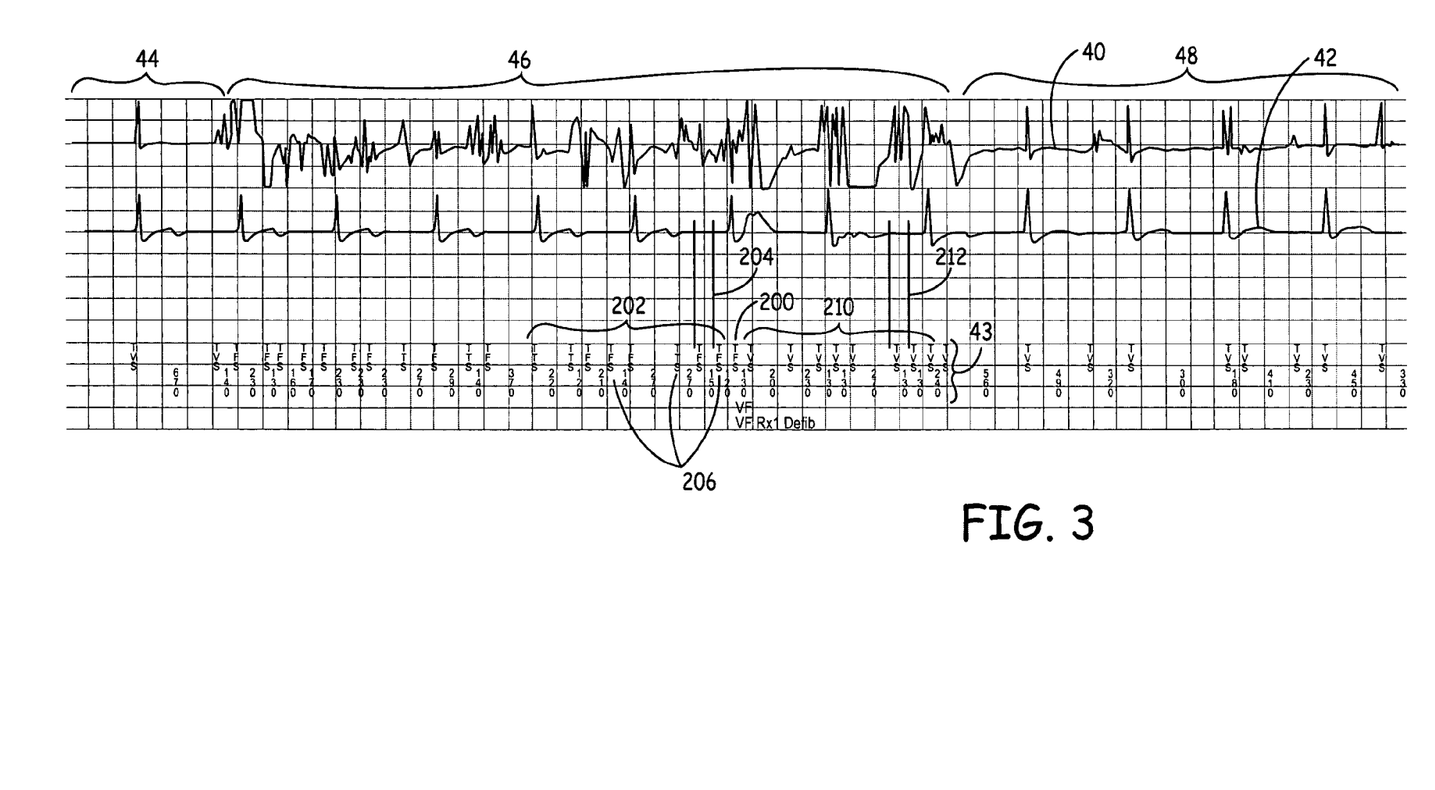
FIG. 3 is a portion of an electrogram showing near-field and far-field R-wave sensing pulses where there is an indication of a false positive near-field pulse.

FIG. 3 is a portion of a stored electrogram showing near-field and far-field pulses where there is an indication of a false positive near-field pulse. As illustrated in FIG. 3, the near-field signal 40 is recorded between the tip and ring electrodes of the bipolar sensing lead, such as electrodes 24 and 26, for example. This signal is input to a sense amplifier that senses voltages that exceed a threshold. The far-field signal 42 is recorded between secondary electrodes such as the lead coil and the can or a sensing lead in another part of the heart (left auricle or right ventricle). A marker channel 43 below far-field electrogram 42 displays each sensed event from the near-field signal, such as Fibrillation Sense (FS), Fibrillation Detected (FD), Tachycardia Sensed (TS) Ventricular Sense (VS) Capacitors charged (CE), or Capacitor Discharged (CD) for example. The numbers below the letters on marker channel 43 indicate the time between sensed events. For example on the left side of FIG. 3 there are two VS events, and the number below and between them is "670", indicating that there were 670 milliseconds between the two VS events. Note that at the left of the electrogram wave 40 is a relatively normal R-wave representation 44. The period of relative normal R-wave representation 44 is followed by a series of erratic signals 46 that indicate an oversensing problem (i.e., a fractured lead conductor or insulation break on the lead).

An examination of far-field signal 42, however, shows a relatively regular far-field R-wave. During the period of relative normal R-wave representation 44, the far-field signal 42 follows the near-field signal 40 quite closely. When the near-field signal 40 becomes erratic in an erratic portion 46, the far-field signal 42 continues to show regular R-wave far-field pulses indicating that the erratic portion 46 may be due to oversensing. As the near-field signal 40 recovers at a period of relative normal R-wave representation 48, the far-field signal 42 continues to follow the near-field signal 40, suggesting that the irregular portion 46 of the near-field signal 40 was due to oversensing, and probably an intermittent failure, since the R-wave pulses of near-field signal 40 recovered at a period of relative normal R-wave representation 48.

With a pattern of this nature, it would be premature to deliver a therapy to the patient, particularly a painful defibrillation shock, in response to erratic portion 46 sensed in far-field signal 40. Typically several methods are used to avoid delivering a shock under these conditions. First, if there is a detection of an irregularity as seen in the erratic portion 46 of near-field signal 40, one can wait to see whether the problem goes away by increasing the number of intervals for detection (as is the case in the waves of FIG. 3), which would suggest that the problem may be an oversensing problem and not an arrhythmia. Also, the sensing lead electrode configuration could be changed, and pacemakers may be programmed to automatically change the sensing lead configuration (e.g. bipolar to unipolar). Finally, the patient could be given an alert (a vibration or audio alert, for example) to advise the patient to see his doctor to have the ICD and its leads checked, but an alert would not prevent the shock at the moment of oversensing.

Figure 4:
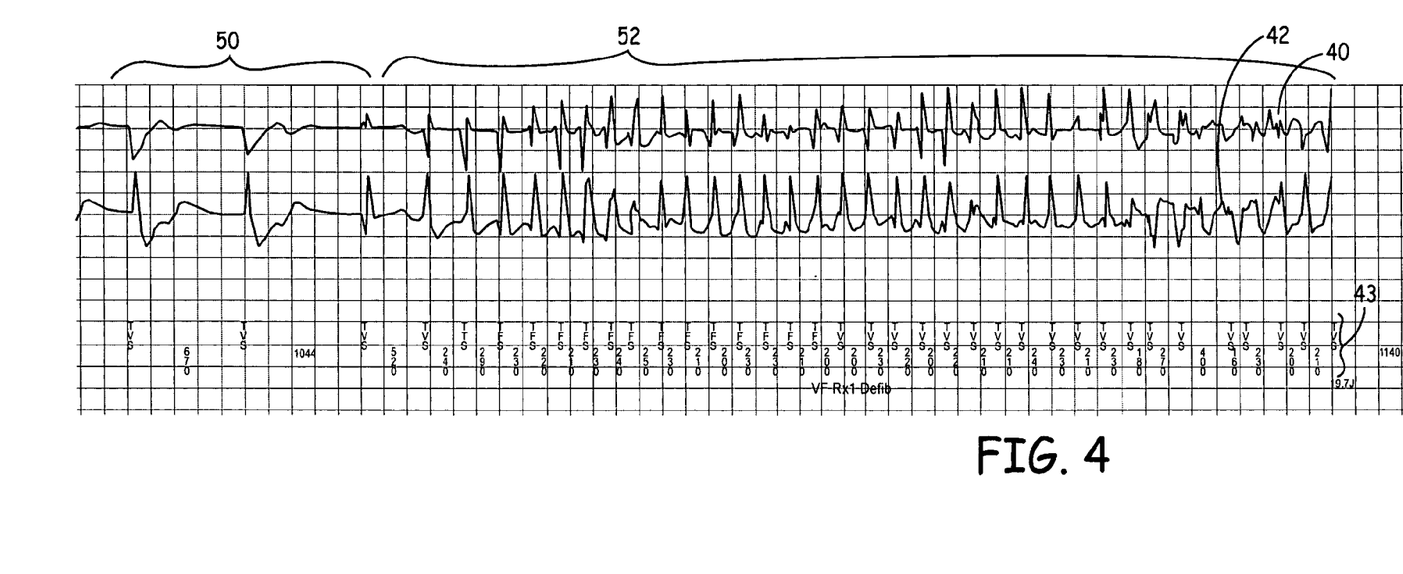
FIG. 4 is a portion of an electrogram showing near-field and far-field R-wave sensing pulses where there is an actual cardiac episode requiring therapy.

FIG. 4 is a portion of an electrogram showing near-field and far-field R-wave sensing pulses where there is an actual cardiac episode requiring therapy. The near-field signal 40 and the far-field signal 42 are shown as in FIG. 3. In this case the beginning (left side) of near-field signal 40 shows relatively normal R-waves in portion 50, although the pulses are inverted from those of FIG. 3. Likewise far-field signal 42 confirms the regularity during portion 50. At portion 52 of the near-field signal 40, however, a highly irregular waveform exists. Unlike in FIG. 3, however, the far-field wave 42 does not maintain a regular R-wave periodicity during portion 50, but rather confirms the irregularity of near-field signal 40. This would strongly suggest an arrhythmia in the patient's ventricle and call for therapy in the form of a defibrillation shock. As above, however, certain intermediate steps may be taken before actually administering the shock such as waiting a short period of time (perhaps ten or fifteen seconds) to see whether the situation resolves itself. This period of time occurs because the capacitors are charging. If in fact this waveform identifies an arrhythmia event, a therapy must be administered very quickly.

The decision to administer a therapy has been based primarily upon the near-field R-wave. The present invention uses the far-field electrogram to discriminate QRS complexes between supraventricular (e.g. sinus tachycardia, atrial fibrillation) and ventricular arrhythmias. In this way, the present invention provides an algorithm that takes into account other information to provide a better determination of an actual arrhythmia before subjecting a patient to a painful defibrillation shock.

Figure 5:
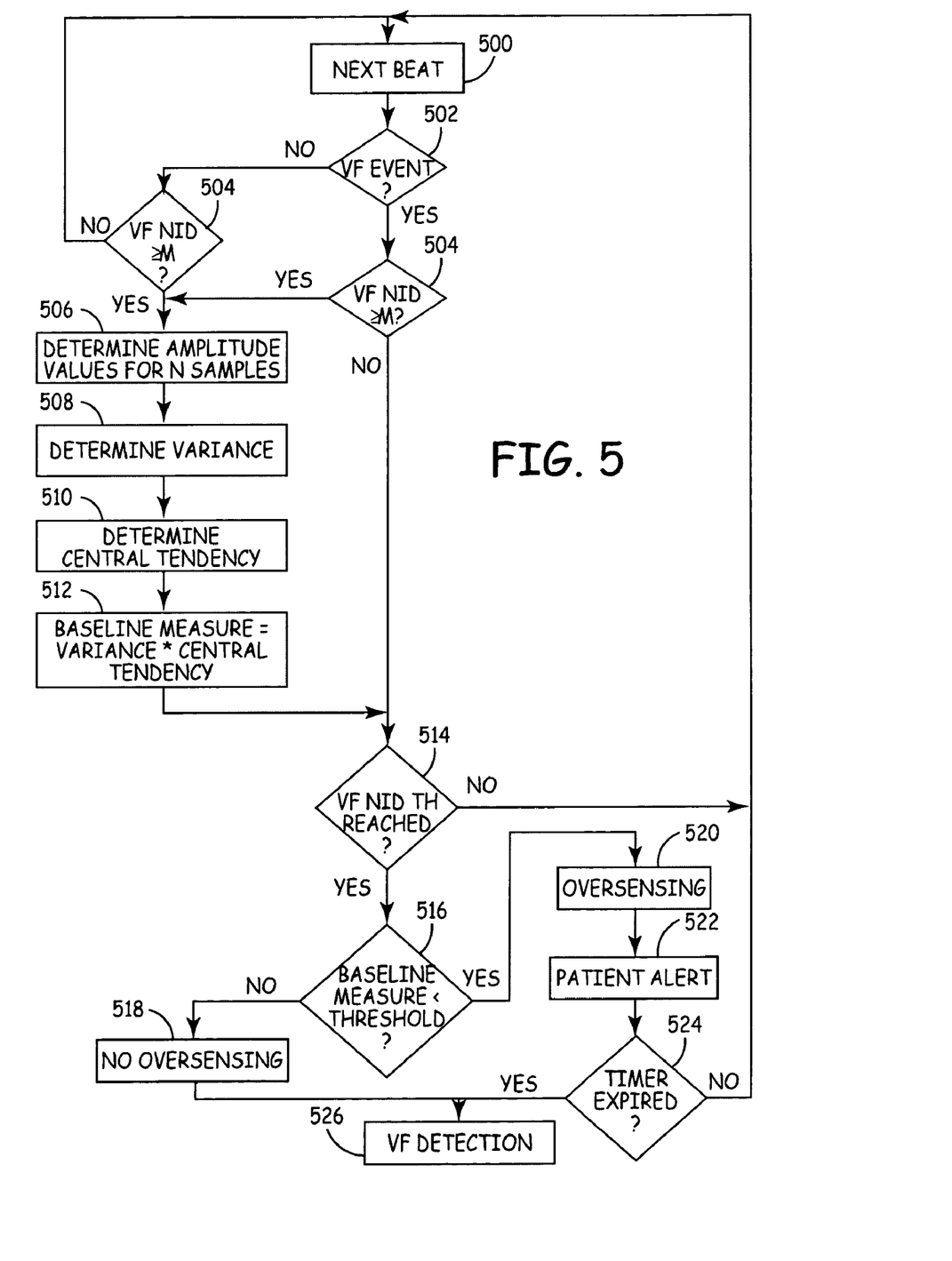
FIG. 5 is a flow chart of a method of delivering a therapy in an implantable medical device, according to an embodiment of the present invention.

FIG. 5 is a flow chart of a method of delivering a therapy in an implantable medical device, according to an embodiment of the present invention. As illustrated in FIG. 5, each time a V-sense signal is sensed between a near-field sensor, i.e., electrodes 24 and 26 corresponding to a next beat, Block 500, a determination is made as to whether the sensed event is a VF event, with a counter corresponding to the number of sensed events and number of VF events being incremented in order to generate a number of intervals for detection of ventricular fibrillation (VF NID), Block 502. In either case, i.e., the event is not a VF event or the event is determined to be a VF event, a determination is made as to whether a predetermined number of VF events M have been detected, Block 504, by determining whether the number of intervals for detection of ventricular fibrillation is greater than the predetermined number M. If the predetermined number of VF events M has not been detected, NO in Block 504, the process waits for the next beat to occur, Block 500. Once the predetermined number of VF events M have been detected, YES in Block 504, a baseline measure associated with a far-field signal associated with the beat that is sensed between secondary electrodes is determined, Blocks 506-512, as described below. The secondary electrodes for sensing the far-field signal can include the lead coil 20 and the uninsulated portion of the housing 11, for example, or a sensing lead 6, 15 in another part of the heart alone or in combination with the uninsulated portion of the housing 11. In addition, the far-field sensing electrodes could also include one of the near-field electrodes.

According to one embodiment of the present invention, for example, the predetermined number M is set as three events so that once three VF events are detected, a baseline measure is determined, Blocks 506-512, for each subsequently sensed beat.

Figure 6A:
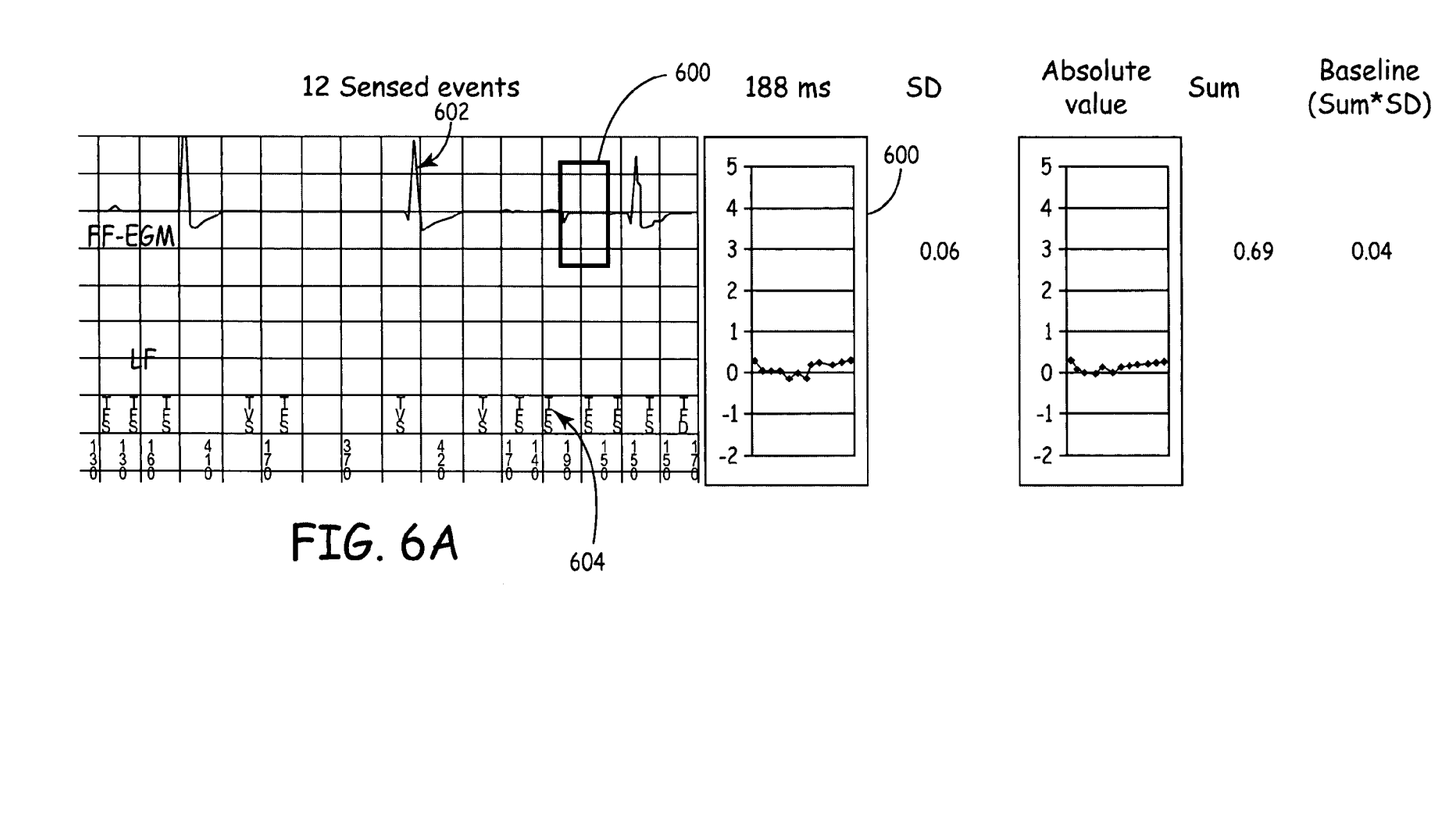
FIGS. 6A and 6B are graphical representations of a determination of a baseline measure of a far-field signal according to an embodiment of the present invention.
Figure 6B:
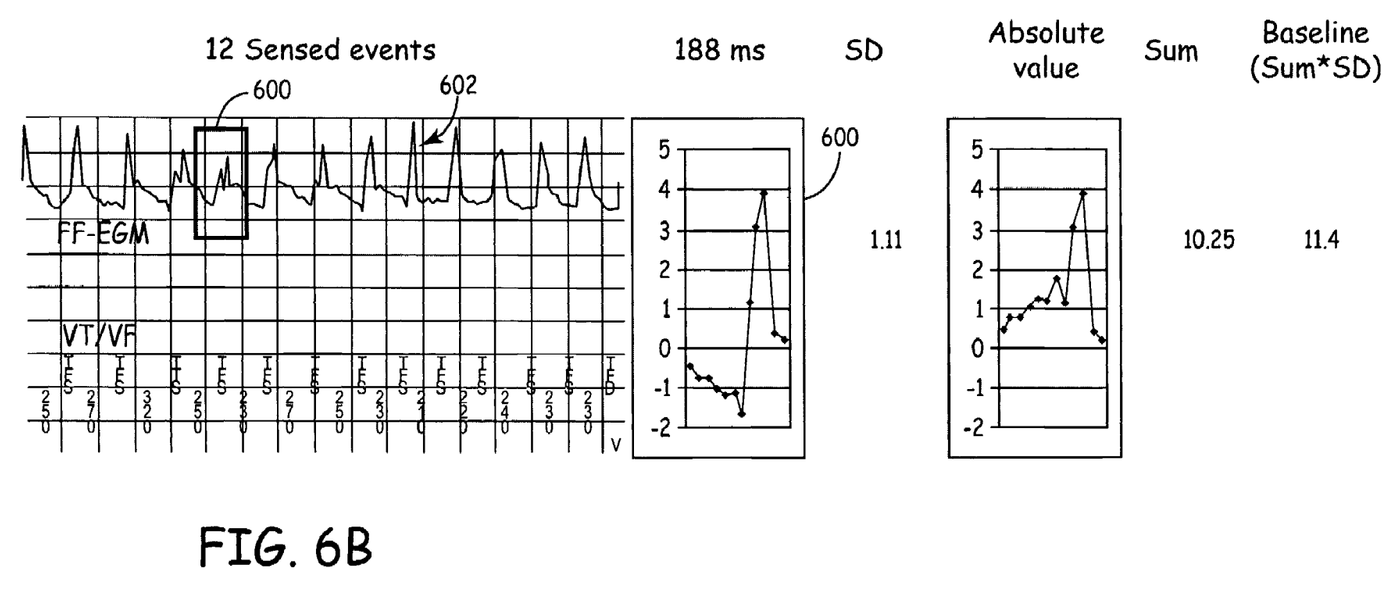

FIGS. 6A and 6B are graphical representations of a determination of a baseline measure of a far-field signal according to an embodiment of the present invention. In particular, as illustrated in FIGS. 5, 6A and 6B, in order to determine the baseline measure for the sensed beats occurring after the predetermined number of VF events M have been detected, voltage values 609 associated with a predetermined number of samples located within a predetermined window 600 of a far-field signal 602 that is centered around the sensed beat 604 are determined, Block 506. According to an embodiment of the present invention, window 600 is set as a 188 ms window, for example, so that voltage values are determined for 12 samples using a 64 Hz sampling rate.

Both a variance, such as a standard deviation SD, for example, of the voltage values of the 12 samples, Block 508, and a central tendency, such as a mean, a median, or a sum, for example, of the absolute values of the voltage values of the twelve samples is determined, and so that the baseline measure is calculated using the product of the variance and the central tendency of the absolute values, Block 512. In addition, according to an embodiment of the present invention, the baseline measure is determined by being set equal to one of either the variance or the central tendency, rather than the product of both.

In addition to determining a baseline measure associated with the current sensed beat, a determination is made as to whether the VF NID is greater than a predetermined threshold, Block 514. For example, according to an embodiment of the present invention, a determination is made in Block 514 as to whether 18 out of the last 24 beats were determined to be VF events. If the VF NID threshold is not reach, NO in Block 514, the process waits for the next beat to be sensed, Block 500. Once the VF NID threshold has been met, YES in Block 514, a determination is made as to whether the baseline measure determined for any of a predetermined number of previously sensed beats, such as the last twelve beats, for example, or for a predetermined number of the 12 beats, such as 2 or 3 of the 12 beats, for example, is less than a predetermined threshold, Block 516. If none of the baseline measures associated with the predetermined number of previously sensed beats is less than the predetermined threshold, NO in Block 516, no oversensing is determined to be occurring and VF detection is confirmed, Block 518. If any one of the baseline measures associated with the predetermined number of sensed beats is less than the threshold, YES in Block 516, oversensing is determined to likely be occurring, Block 520, such as would result from a lead integrity failure, for example, and a patient alert, such as a vibration or audio alert, a wireless signal transmitted to a remote monitor, satellite, internet, for example, is activated to alert the patient, Block 522, and to advise the patient to see his doctor to have the ICD and its leads checked. Because the alert is not intended to prevent the shock at the moment of oversensing, the process is repeated for the next beat, Block 500, until a predetermined time period associated with the charging of the capacitor(s) for delivering the shock, such as 10 seconds, for example, has expired, YES in Block 524. Once the timer has expired, the VF detection process for delivering a corresponding shock therapy continues according to the normal VF detection process, Block 526, and therapy is delivered as determined necessary.

According to an embodiment of the invention, once it is determined that the patient is experiencing a VF event, i.e., the VF NID is greater than the threshold (18 of last 24 beats are determined to be VF events) and oversensing is determined, the device begins charging of one or more capacitors for delivering the therapy to the patient. According to another embodiment of the invention, once it is determined that oversensing is likely to be occurring, charging of the capacitors may be withheld until the timer of Block 524 has expired, for example. In this way, the algorithm of the present invention checks to see if the baseline measure threshold has been satisfied for each beat at and after VF detection, withholding charging and/or therapy until either the threshold is not satisfied or the timer expires.

As illustrated in FIGS. 6A and 6B, in order to reduce the effects of oversensing, the present invention evaluates the corresponding far-field signal to determine whether a VF episode is also indicated in the far-field signal, so that if the VF NID threshold is met in Block 516 due to oversensing rather than the occurrence of a VF episode, such as when there is a loss in lead integrity resulting from lead fractures, corrupted connector interfaces, EMI issues, R-wave oversensing, myopotentials, etc., the patient is alerted of the possible oversensing issue. In particular, when VF is detected in the signal sensed by the near-field sensor but not in the signal detected by the far-field sensor 602, both the standard deviation of the voltage values of the samples in the associated window 600 and the absolute values of the voltage values will be negligible since the far-field signal will likely approach the isoelectric baseline value of the far-field EGM signal, as illustrated in FIG. 6A. However, when VF is detected both in the signal sensed by the near-field sensor and in the signal detected by the far-field sensor 602, both the standard deviation of the voltages of the samples in the associated window 600 and the absolute values of the voltages will be greater. Therefore the product of the standard deviation and the sum of the absolute values, Block 512, will be small when there is oversensing compared to when an actual arrhythmia event is occurring. In particular, according to an embodiment of the present invention, the threshold of Block 516 is set equal to one, so that if the product of the standard deviation and the sum of the absolute values is less than one for any of the predetermined number of previously sensed events, it is likely that the isoelectric baseline of the far-field signal is occurring and therefore oversensing is likely occurring.

Some of the techniques described above may be embodied as a computer-readable medium comprising instructions for a programmable processor such as microprocessor 224. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for delivering therapy in an implantable medical device according to the present invention.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method of determining oversensing in a medical device, comprising:
    sensing a first cardiac signal and detecting cardiac events via a first electrode configuration;
    determining the presence of an episode requiring therapy in response to the detected cardiac events;
    sensing the first cardiac signal via a second electrode configuration;
    determining a variance of samples associated with the first cardiac signal sensed via the second electrode configuration;
    determining a central tendency associated with the samples; and
    determining whether to deliver therapy in response to the determined variance and the determined central tendency.

2. The method of claim 1, further comprising:
    determining whether a threshold number of the detected cardiac events are determined to be an episode requiring therapy; and
    determining, in response to the predetermined number of the detected cardiac events being determined to be an episode requiring therapy, whether the determined variance and the determined central tendency are indicative of an isoelectric baseline, wherein determining the presence of an episode requiring therapy comprises determining whether a predetermined number of the detected cardiac events correspond to an episode requiring therapy.

3. The method of claim 2, wherein the threshold number of the detected cardiac events is 18 out of 24 events and the predetermined number of detected cardiac events is three events.

4. A method of determining oversensing in a medical device, comprising:
    sensing a first cardiac signal and detecting cardiac events via a first electrode configuration;
    determining the presence of an episode requiring therapy in response to the detected cardiac events;
    sensing the first cardiac signal via a second electrode configuration;
    determining baseline measurements of samples of the first cardiac signal sensed via the second electrode configuration; and determining whether to deliver therapy in response to the baseline measurement, wherein determining the baseline measurement comprises:
    determining a variance of voltage values of the samples; and
    determining a central tendency of the voltage values of the samples, wherein the therapy is delivered in response to the product of the variance and the central tendency being greater than a predetermined threshold.

5. The method of claim 4, further comprising generating a patient alert in response to the product of the variance and the central tendency being less than or equal to the predetermined threshold.

6. The method of claim 5, wherein the predetermined threshold is one.

7. The method of claim 5, further comprising suspending delivery of the therapy for up to a predetermined time period in response to the product of the variance and the central tendency being less than or equal to the predetermined threshold.

8. A medical device, comprising:
    means for sensing a first cardiac signal and detecting cardiac events via a first electrode configuration;
    means for determining the presence of an episode requiring therapy in response to the detected cardiac events;
    means for sensing the first cardiac signal via a second electrode configuration;
    means for determining a variance of samples associated with the first cardiac signal sensed via the second electrode configuration;
    means for determining a central tendency associated with the samples; and
    means for determining whether to deliver therapy in response to the determined variance and the determined central tendency.

9. The device of claim 8, further comprising:
    means for determining whether a threshold number of the detected cardiac events are determined to be an episode requiring therapy; and
    means for determining, in response to the predetermined number of the detected cardiac events being determined to be an episode requiring therapy, whether the determined variance and the determined central tendency are indicative of an isoelectric baseline, wherein means for determining the presence of an episode requiring therapy comprises means for determining whether a predetermined number of the detected cardiac events correspond to an episode requiring therapy.

10. The device of claim 9, wherein the threshold number of the detected cardiac events is 18 out of 24 events and the predetermined number of detected cardiac events is three events.

11. A medical device, comprising:
    means for sensing a first cardiac signal and detecting cardiac events via a first electrode configuration;
    means for determining the presence of an episode requiring therapy in response to the detected cardiac events;
    means for sensing the first cardiac signal via a second electrode configuration;
    means for determining a baseline measurement of samples of the first cardiac signal sensed via the second electrode configuration; and means for determining whether to deliver therapy in response to the baseline measurement, wherein means for determining the baseline measurement comprises:
    means for determining a variance of voltage values of the samples; and means for determining a central tendency of the voltage values of the samples, wherein the therapy is delivered in response to the product of the variance and the central tendency being greater than a predetermined threshold.

12. The device of claim 11, further comprising means for generating a patient alert in response to the product of the variance and the central tendency being less than or equal to the predetermined threshold.

13. The device of claim 12, wherein the predetermined threshold is one.

14. The method of claim 12, further comprising means for suspending delivery of the therapy for a predetermined time period in response to the product of the variance and the central tendency being less than or equal to the predetermined threshold.

15. A computer readable medium having computer executable instructions for performing a method comprising:
   sensing a first cardiac signal and detecting cardiac events via a first electrode configuration;
   determining the presence of an episode requiring therapy in response to the detected cardiac events;
   sensing the first cardiac signal via a second electrode configuration;
   determining a variance of samples associated with the first cardiac signal sensed via the second electrode configuration;
   determining a central tendency associated with the samples; and
   determining whether to deliver therapy in response to the determined variance and the determined central tendency.

16. The computer readable medium of claim 15, wherein the therapy is delivered in response to the product of the variance and the central tendency being greater than a predetermined threshold.

17. The computer readable medium of claim 16, further comprising generating a patient alert in response to the product of the variance and the central tendency being less than or equal to the predetermined threshold.

18. The computer readable medium of claim 15, further comprising suspending delivery of the therapy for a predetermined time period in response to the product of the variance and the central tendency being less than or equal to the predetermined threshold.

19. The computer readable medium of claim 15, further comprising:
   determining whether a threshold number of the detected cardiac events are determined to be an episode requiring therapy; and
   determining, in response to the predetermined number of the detected cardiac events being determined to be an episode requiring therapy, whether the baseline measurement is indicative of an isoelectric baseline, wherein determining the presence of an episode requiring therapy comprises determining whether a predetermined number of the detected cardiac events correspond to an episode requiring therapy.

* * * * *